US008003596B2

(12) United States Patent
Appeldoorn et al.

(10) Patent No.: US 8,003,596 B2
(45) Date of Patent: Aug. 23, 2011

(54) P-SELECTIN TARGETING LIGAND AND COMPOSITIONS THEREOF

(75) Inventors: Chantal Catharina Maria Appeldoorn, Leiden (NL); Theodorus Josephus Cornelis Van Berkel, Leiden (NL); Erik Anna Leonardus Biessen, Leiden (NL)

(73) Assignee: Astellas Pharma Inc., Tokyo (JP)

( * ) Notice: Subject to any disclaimer, the term of this patent is extended or adjusted under 35 U.S.C. 154(b) by 1177 days.

(21) Appl. No.: 10/558,492

(22) PCT Filed: Jun. 1, 2004

(86) PCT No.: PCT/EP2004/005873
§ 371 (c)(1),
(2), (4) Date: Nov. 29, 2006

(87) PCT Pub. No.: WO2004/105783
PCT Pub. Date: Dec. 9, 2004

(65) Prior Publication Data
US 2007/0185348 A1 Aug. 9, 2007

(30) Foreign Application Priority Data
May 30, 2003 (EP) .................................... 03012123

(51) Int. Cl.
*A61K 38/00* (2006.01)
*A61K 51/00* (2006.01)
(52) U.S. Cl. .......................... 514/1.1; 530/300; 424/1.69
(58) Field of Classification Search .................. None
See application file for complete search history.

(56) References Cited

U.S. PATENT DOCUMENTS
6,583,301 B1  6/2003  Eaton et al.

FOREIGN PATENT DOCUMENTS
| EP | 1 288 222 A1 | 3/2003 |
| WO | 99/52858 A2 | 10/1999 |
| WO | 01/12154 A2 | 2/2001 |
| WO | 01/60416 A2 | 8/2001 |
| WO | 02/26776 A2 | 4/2002 |
| WO | 02/055111 A2 | 7/2002 |
| WO | 02/098951 A2 | 12/2002 |
| WO | WO 02/098952 A1 | 12/2002 |
| WO | 03/020753 A1 | 3/2003 |

OTHER PUBLICATIONS

Molenaar et al. Specific inhibition of P-selectin-mediated cell adhesion by phage display-derived peptide antagonists. Blood (2002), 100(10), 3570-3577.*
International Preliminary Examination Report on Patentability for PCT/EP2004/005873 dated Dec. 1, 2005.
Geng, J. et al., "Lectin Domain Peptides from Selectins Interact with Both Cell Surface LigandS and Ca2+ Ions", *The Journal of Biological Chemistry*, 1992, vol. 267, No. 28, Issue of Oct. 5, pp. 19846-19853.
Chamoun, F. et al., "Pathophysiologic Role of Selectins and Their Ligands in Ischemia Reperfusion Injury", *Frontiers in Bioscience 5*, Nov. 1, 2000, pp. 103-109.
Everts, M. et al., "Selective Intracellular Delivery of Dexamethasone into Activated Endothelial Cells Using an E-Selectin-Directed Immunoconjugate", *The Journal of Immunology*, 2002, vol. 168, pp. 883-889.
Hayashi, S. et al., "Roles of P-Selectin in Inflammation, Neointimal Formation, and Vascular Remodeling in Balloon-Injured Rat Carotid Arteries", *Circulation*, 2000, vol. 102, pp. 1710-1717.
Maruyama, K., "PEG-Immunoliposome", *Bioscience Reports*, Apr. 2002, vol. 22, No. 2, pp. 251-266.
Spragg, D. et al., "Immunotargeting of Liposomes to Activated Vascular Endothelial Cells: A Strategy for Site-Selective Delivery in the Cardiovascular System", *Proc. Natl. Acad. Sci. USA*, Aug. 1997, vol. 94, pp. 8795-8800.
Panés, J., "Adhesion Molecules in Inflammatory Bowel Disease", *Pathophysiology 5*, 1999, 271-282.

* cited by examiner

*Primary Examiner* — Maury Audet
(74) *Attorney, Agent, or Firm* — McDonnell Boehnen Hulbert & Berghoff LLP

(57) ABSTRACT

P-selectin targeting ligand molecules are provided as well as compositions, including kits, which comprise such P-selectin targeting ligand molecules, such composition being useful for use as pharmaceutical formulations which can be administered safely and effectively and as diagnostic formulations.

18 Claims, No Drawings

P-SELECTIN TARGETING LIGAND AND COMPOSITIONS THEREOF

The present invention relates to P-selectin targeting ligands and compositions containing such ligands, including kits.

BACKGROUND OF THE INVENTION

Inflammation and inflammatory processes play a major role in the pathophysiology of numerous diseases and conditions. Conditions of the brain in which increased levels of inflammation mediators were found include severe traumatic brain injury, relapsing-remitting multiple sclerosis, cerebral artery occlusion, ischemia, and stroke. Conditions of the heart in which mediators such as the selectins are suggested to play a role include acute myocardial infarct, arterial injury, such as produced by angioplasty, and ischemia. Similarly, selectins are involved in conditions of the kidneys, such as renal injury from ischemia and reperfusion, and renal failure. Furthermore, selectins appear to play a role in organ transplant rejection, cold ischemia, hemorrhagic shock, septic shock, tumour metastasis, chronic inflammation, rheumatoid arthritis, inflammatory bowel disease, atherosclerosis, restenosis, angiogenesis, disseminated intravascular coagulation, adult respiratory stress syndrome, and circulatory shock.

Cell surface adhesion molecules have become recognised as key mediators in numerous cellular processes including cell growth, differentiation, immune cell transmigration and response, and cancer metastasis. Four major categories of adhesion molecules have been identified: the immunoglobulin superfamily cell adhesion molecules (CAMs), cadherins, integrins, and selecting. The selectins represent a family of presently three transmembraneous, carbohydrate-binding glycoproteins: "endothelial" E-selectin, "leukocyte" L-selectin, and "platelet" P-selectin. All three selectins are divalent cation (e.g. calcium) dependent and possess an extracellular domain with a carbohydrate recognition motif, an epidermal growth factor-like motif, and some smaller domains related to complement-regulatory proteins.

Human P-selectin (also referred to as GMP-140, LECAM-3, PADGEM, CD62, CD62P) is expressed by platelets and endothelial cells. When expressed on these cell surfaces, its most notable effect is the slowing of leukocytes as these leave the capillaries and enter the postcapillary venules, the latter representing the major site of leukocyte-endothelium adhesion. The slowing process is observed as leukocyte rolling, signifying an initial adhesion with relatively low affinity. The firm adhesion of rolling leukocytes is primarily mediated by integrins.

In endothelial cells, P-selectin is stored on Weibel-Palade bodies; in platelets, it is found in the α-granules. Following activation, P-selectin is mobilised to the cell surfaces within a few minutes in response to a variety of inflammatory or thrombogenic agents. The endothelial P-selectin's primary function is to recruit leukocytes into postcapillary venules, while platelet P-selectin also results in the formation of thrombi. One of the presently known natural ligands of P-selectin is PSGL-1 (P-selectin glycoprotein ligand-1), a 160 kDa sialoprotein expressed on the surface of leukocytes where it is concentrated at the uropod. More detailed descriptions of the structure and functions of p-selectin are found in numerous publications, such as J. Panes, Pathophysiology 5: 271 (1999); F. Chamoun et al., Frontiers in Bioscience 5: e103 (Nov. 1, 2000); S.-I. Hayashi, Circulation 102: 1710 (2000).

P-selectin also appears to be involved more directly in platelet aggregation, as was shown recently by studies of the Ca-independent interactions of P-selectin with 3-sulfated galactosyl ceramide (also referred to as sulfatides). This interaction probably takes place at a different binding site of P-selectin, as the binding can be inhibited by the antibody WASP12.2, but not by AK4, whereas the binding of the natural P-selectin ligand PSGL-1, which is involved in leukocyte adhesion, is blocked by both WASP12.2 and AK4. However, it appears that the binding sites are overlapping. It is assumed that sulfatide interactions stabilise platelet aggregates.

On the one hand, it would seem feasible to improve these and other conditions involving the activation of endothelial cells and leukocytes, and specifically the mobilisation and expression of P-selectin by specifically interrupting the P-selectin cascades. This can be done, for instance, by the administration of ligands which selectively bind to human P-selectin, but which do not possess its bioactivity. By this method, mobilised P-selectin could be inactivated and leukocyte-induced tissue damage prevented. Potentially, the same effect could be achieved by gene therapy, provided the P-selectin ligand or antagonist is a peptide or modified peptide. According to this method, somatic cells of a person in need of the therapy would be transfected with an expression vector carrying a DNA sequence encoding a P-selectin antagonist.

On the other hand, P-selectin-related diseases and conditions may also be treated or prevented by drugs which do not directly interact with P-selectin, but which suppress some of the detrimental effects of P-selectin activation in the respective cells and tissues. Among the drug substances potentially useful for therapeutic intervention are anti-inflammatory agents such as glucocorticoids.

One of the major drawbacks of any systemic therapy with highly active compounds is their distribution within the organism and the exposure of unaffected cells and tissues, potentially leading to substantial side effects. It would be most desirable to have methods and drug delivery systems available which allow the targeted delivery of active agents specifically to affected cells, without substantially exposing unaffected cells.

While there is no pharmaceutical product comprising a cell-specifically targeted drug delivery system available on the market today, a number of experimental delivery systems have been described in the scientific and patent literature. Drug targeting may be based on conjugates of active principles with target-recognising ligands, such conjugates representing molecular drug delivery systems. A general disadvantage of such conjugates is the low ration of drug substance per ligand (often only 1:1), resulting in the exposure to high levels of ligands.

As an example, Everts et al. (J. Immunol. 168: 883 (2002)) report the selective intracellular delivery of dexamethasone into activated endothelial cells using an E-selectin-directed immunoconjugate. Dexamethasone was covalently attached to an anti-E-selectin Ab, resulting in the so-called dexamethasone-anti-E-selectin conjugate. Binding of the conjugate to E-selectin was studied using surface plasmon resonance and immunohistochemistry. Furthermore, internalisation of the conjugate was studied using confocal laser scanning microscopy and immuno-transmission electron microscopy. It was demonstrated that the dexamethasone-anti-E-selectin conjugate, like the unmodified anti-E-selectin Ab, selectively bound to TNF-alpha-stimulated endothelial cells and not to resting endothelial cells. After binding, the conjugate was internalised and routed to multivesicular bodies, which is a lysosome-related cellular compartment. After intracellular degradation, pharmacologically active dexamethasone was released, as shown in endothelial cells that were transfected with a glucocorticoid-responsive reporter gene. Furthermore, intracellularly delivered dexamethasone was able to down-regulate the proinflammatory gene IL-8.

Alternatively, carrier-based drug delivery systems may be rendered target-specific by attaching appropriate target-recognising ligands to their surface. For instance, this approach has been employed using liposomes as carriers. Some of the recent developments based on this approach have been reviewed by Maruyama (Biosci. Rep. 22: 251 (2002)).

For instance, methods for E-selectin targeted drug delivery have been investigated by Spragg et al. (Proc. Nat. Acad. Sci USA 94: 8795 (1997)). According to this document, E-selectin was selected as a molecular target for endothelial-selective delivery of therapeutic drugs or genes for treating various disease states. Liposomes of various types (classical, sterically stabilised, cationic, pH-sensitive), each conjugated with mAb H18/7, a murine monoclonal antibody that recognises the extracellular domain of E-selectin, bound selectively and specifically to IL-1 beta-activated HUVEC at levels up to 275-fold higher than to unactivated HUVEC. E-selectin-targeted immunoliposomes appeared in acidic, perinuclear vesicles 2-4 hr after binding to the cell surface, consistent with internalisation via the endosome/lysosome pathway. Activated HUVEC incubated with E-selectin-targeted immunoliposomes, loaded with the cytotoxic agent doxorubicin, exhibited significantly decreased cell survival, whereas unactivated HUVEC were unaffected by such treatment.

On the other hand, there is some evidence that P-selectin may also be at least as an appropriate molecular target for activated endothelial cell involved in inflammatory processes, as was described above. Therefore, there is a need for drug delivery systems which are specifically targeted to this member of the selectin family, and thereby to cells and tissues showing (increased) P-selectin expression or presentation.

The majority of P-selectin binding compounds known today are carbohydrates, based on sialyl Lewis X (sLeX), a tetrasaccharide and natural ligand for the selecting. However, these mimics have the disadvantage of displaying low affinity (micromolar to millimolar range) and low specificity, as they tend to bind to other members of the selectin family with approximately the same affinity as they have for P-selectin.

Therefore, there also is a need for such P-selectin-directed, targeted drug delivery systems which have a high affinity and specificity for the target molecule.

SUMMARY OF THE INVENTION

It is an object of the invention to provide P-selectin targeting ligand molecules.

It is a further object of the invention to provide compositions which comprise such P-selectin targeting ligand molecules, such composition being useful for use as pharmaceutical formulations which can be administered safely and effectively and as diagnostic formulations.

In another aspect, it is an object of the invention to provide kits for the preparation of such compositions.

DETAILED DESCRIPTION OF THE INVENTION

In a first aspect, the invention provides a targeting ligand molecule comprising:
a target-recognising moiety
a spacer, which is formed from a water soluble oligomer or polymer and
an anchoring moiety, which is formed from an amphiphilic lipid, consisting of at least one hydrophobic apolar moiety and a hydrophilic polar head group, wherein the target recognising moiety is derived from:

(1) a peptide, peptoid or derivative thereof having an amino acid sequence $X(A_x)_m A_3 A_1 A_2 A_1 Y$, or a functional equivalent of said sequence, wherein:

$A_1$ is a D- or L-cysteine (C), D- or L-valine (V) or an analogue or mimetic thereof;

$A_2$ is a D- or L-aspartic acid (D) or an analogue thereof;

$A_3$ is a D- or L-phenylalanine (F), or D- or L-tryptophan (W) or an analogue or mimetics thereof;

$A_x$ is a D- or L-amino acid, selected from the group consisting of glutamic acid (E), aspartic acid (D), glycine (G) and cysteine (C) and analogues or mimetics thereof;

X marks the N-terminal side of said sequence and is hydrogen or a residue comprising 1 to 6 D- or L-amino acids or analogues thereof;

Y marks the C-terminal side of said sequence and is —OH or a residue comprising 1 to 11 D- or L-amino acids or analogues thereof;

wherein X and Y together can form a cyclic system;

characterised in that at least one of X and Y or X+Y is substituted with the group $R^1$—$(Z)_n$— wherein:

Z is selected from —CO—, —O—, —NR²—, and —CO—NR²—;

$R^1$ and $R^2$ are independently selected from:

a) H;

b) a $C_1$-$C_8$ alkyl group;

c) a $C_2$-$C_8$ alkyl group, wherein at least one C-atom is replaced with a nitrogen-, oxygen- or sulphur atom;

d) a $C_6$-$C_{14}$ aryl group, which may be substituted with at least one group selected from a halogen, $C_1$-$C_6$-alkyl, —CF₃, —OH, —O—$C_1$-$C_6$-alkyl, —COOH, —COO—$C_1$-$C_6$-alkyl, —NO₂, —NH₂, —NH—$C_1$-$C_6$-alkyl, —N—($C_1$-$C_6$-alkyl)₂ and —SO₃H;

e) a heteroaryl group which is selected from 5- or 6-membered ring systems and benzo-condensed ring systems, and has at least one heteroatom selected from the group consisting of nitrogen, oxygen and sulphur, wherein said heteroaryl group may be substituted with at least one group selected from the group consisting of a halogen, —$C_1$-$C_6$-alkyl, —CF₃, —OH, —O—$C_1$-$C_6$-alkyl, —COOH, —COO—$C_1$-$C_6$-alkyl, —NO₂, —NH₂, —NH—$C_1$-$C_6$-alkyl, —N—($C_1$-$C_6$-alkyl)₂ and —SO₃H;

f) an aralkyl group comprising an alkyl group as defined in b) or c) and an aryl group or heteroaryl group as defined in d) or e); and m and n are an integer independently selected from 0 and 1, with the proviso that n is not 0 when $R^1$ is H.

(2) a compound represented by the following formula Ia:

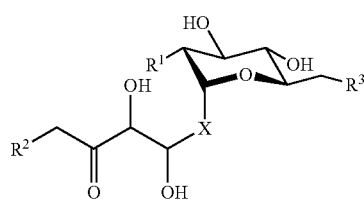

and its stereo-isomer, represented by the following formula Ib:

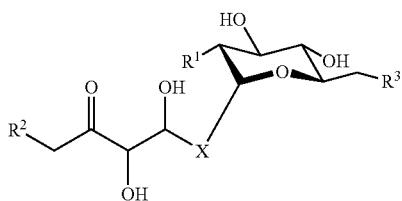

wherein:
X is an optional group, which represents —O—, —OCH$_2$—, —S—, —SCH$_2$—, —NH— or —NHCH$_2$—;
R$^1$ represents QR$^4$, wherein Q represents —O—, —NH—, —NH—(C=O)—, —O—(C=O), —NH—(C=O)—O— or —NH—(C=O)—NH—; and wherein R$^4$ represents H or any compound comprising at least one carbon atom;
R$^2$ is a moiety bearing at least one negative charge and R$^3$ can be any group,
provided that if Q=—O— and R$^4$ is —H—, X is present.
(3) gallic acid or a derivative thereof, a polyphenol or a polyhydroxy phenol of structural formula II:

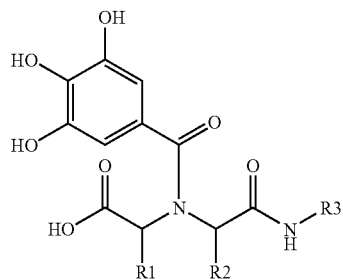

characterised in that:
R$^1$=a hydrogen; a straight or branched (C$_1$-C$_4$) aliphatic alkyl group or an aromatic group, optionally respectively substituted by a hydroxyl group, a carboxylic acid group, an amino group or a straight or branched (C$_1$-C$_4$) aliphatic alkyl group;
R$^2$=an optional group, being a straight or branched (C$_1$-C$_4$) aliphatic alkyl group;
R$^3$=a straight or branched (C$_1$-C$_4$) aliphatic alkyl group, optionally substituted by one or more carboxylic acid group, or a straight or branched (C$_1$-C$_4$) aliphatic alkyl amide group; or
a (C$_3$-C$_8$) cycloalkyl group, optionally substituted by a straight or branched (C$_1$-C$_4$) aliphatic alkyl group or one or more carboxylic acid group.
Preferred as targeting ligand molecules are compounds with selective affinity for P-selectin.
In these molecules the target recognising moiety can be derived from a peptide, peptoid or derivative thereof.
Peptides are defined as amides that are derived from two or more amino acids by combination of the amino group of one acid with the carboxyl group of another (Merriam Webster Medical Dictionary 2001). As used herein, a peptide may also refer to a peptidic structure within a molecule. Typically, peptides are composed of naturally occurring L-α-amino acids, which are alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

Functional equivalents of the peptides of the invention are proteinaceous molecules, comprising the same human P-selectin binding activity in kind, but not necessarily in amount, and may, for instance, be modified peptides, peptoids, peptide analogues or peptidomimetics.

Modified peptides are molecules derived from peptides by the introduction of substituents or functional groups which are not present in naturally occurring amino acids. The term also includes compounds which are obtained by the reaction of peptides with molecules from other chemical categories, whether these molecules a naturally occurring or not. For instance, biotinylated peptides, glycoproteins, and lipoproteins are frequently found in nature, while peptides modified with polyethylene glycol, such as pegylated interferons, are examples of chemically modified peptides that have been designed to alter some, but not all of the peptides' properties.

Peptoids, like peptides, are typically amides of two or more amino acids. However, they are frequently not directly derived from naturally occurring amino acids, but rather of various types of chemically synthesised L- or D-amino acids.

Peptidomimetics, in their broadest scope, are compounds which are in their functional structure more or less similar to a peptide, but which may also contain non-peptidic bonds in the backbone, or D-amino acids. In general, peptidomimetics serve as substitutes for native peptides in the interaction with receptors and enzymes (Pharmaceutical Biotechnology, Ed. D. J. A. Crommelin and R. D. Sindelar, Harwood Academic Publishers, 1997, p. 138). Pseudopeptides, a class of peptidomimetics, are compounds containing amide bond isoesters instead of amide bonds (ibid., pp. 137-140).

Peptidic ligands of the invention also include salts of peptides or functional equivalents, such as pharmaceutically acceptable acid- or base addition salts.

Preferred peptidic targeting ligands comprise a target recognising moiety with the amino acid sequence XA$_x$A$_3$A$_1$A$_2$A$_1$Y, or a functional equivalent of said sequence, wherein A$_1$ is a D- or L-cysteine (C), D- or L-valine (V) or an analogue thereof; A$_2$ is a D- or L-aspartic acid (D) or an analogue or mimetic thereof; A$_3$ is a D- or L-phenylalanine (F), D- or D- or L-tryptophan (W) or an analogue or mimetic thereof; A$_x$ is a D- or L-amino acid, selected from the group consisting of glutamic acid (E), aspartic acid (D), glycine (G) and cysteine (C) and analogues or mimetics thereof; and wherein X marks the N-terminal side of said sequence and is hydrogen or a residue comprising 1 to 6 D- or L-amino acids or analogues thereof; Y marks the C-terminal side of said sequence and is —OH or a residue comprising 1 to 11 D- or L-amino acids or analogues thereof; wherein X and Y together can form a cyclic system. In one of the particularly preferred embodiments, the ligands comprise the amino acid sequence XEWVDVY, or a functional equivalent of this sequence. Peptidic compounds comprising this amino acid sequence have been described in more detail in WO 03/020753 and in WO 04/018502, whose disclosure is incorporated herein by reference and to which disclosure the reader is specifically referred for details regarding the manufacturing.

The targeting recognising moiety can also be derived from the chemical compounds, as disclosed in WO 04/033473 and in not pre-published international patent application PCT/EP04/004898.

The compounds as disclosed in WO 04/033473 are represented by the formula Ia and Ib in this application. These glucose-based compounds are characterised in that they possess a substituent $R^1$ at the C-2 of the monosaccharide structure. This substituent $R^1$ is much more critical than substituent $R^3$. Without wishing to be bound by any theory, it is believed that $R^1$ plays an active role in the recognition of or selectivity to P-selectin. $R^1$ represents $QR^4$, wherein Q represents —O—, —NH—, —NH—(C=O)—, —O—(C=O), —NH—(C=O)—O— or —NH—(C=O)—NH and preferably —NH—(C=O)—; and wherein $R^4$ represents any substituent comprising at least one carbon atom. Preferred groups $R^4$ are linear or branched alkyl or aryl groups, linear or branched aralkyl or alkaryl groups, which groups can contain one or more heteroatoms, such as nitrogen, oxygen, phosphorous, sulphur atoms, and which groups preferably have up to 20 carbon atoms, more preferably between 1 and 12 carbon atoms; the groups can be substituted with halogen atoms, hydroxyl groups, oxygen atoms, alkoxy and aryloxy groups, amino or substituted amino groups, as well as other substituents. In especially preferred embodiments, the electron withdrawing groups are present on the aromatic moieties. Most preferably $R^4$ is H, an alkyl moiety, an aromatic moiety or an electron withdrawing moiety.

The aromatic moiety can, for example, be a phenyl, naphthyl, cresyl, tolyl, anthracyl, phenanthryl, pyridyl, pyrazyl, pyridazyl or quinolyl group, which group can optionally be substituted. Preferably, $R^4$ is a phenyl or naphthyl group.

In another embodiment, $R^4$ is a group comprising an electron-withdrawing moiety. Preferably, the electron withdrawing moiety is a moiety selected from the group consisting of nitro, —(C=O)-alkyl, cyanonitrile, —SO$_3$H, CCl$_3$ or CF$_3$; more preferably, the electron withdrawing group is a nitro group.

In this invention further compounds from which the targeting recognising moiety can be derived are gallic acid and derivatives thereof, polyphenols and polyhydroxy phenols as described in not prepublished international patent application PCT/EP04/004898.

Gallic acid, or 3,4,5-trihydroxybenzoic acid, is a natural polyhydroxy phenol found in fruits, vegetables and herbs, such as in gall nuts, walnuts, mango seeds, red grapes, green tea and olive oil. In many plant products gallic acid is contained in the form of precursors such as tannic acid, also named tannin or gallotannin, which describes a class of compounds with a complex and non-uniform chemical structure. Tannins may be divided into 2 groups: (a) derivatives of flavanols, so-called condensed tannins and (b) hydrolysable tannins (the more important group) which are esters of a sugar, usually glucose, with one or more trihydroxybenzenecarboxylic acids. Gallic acid is a major hydrolysis product of tannin. Further, the targeting recognising moiety can be derived from gallic acid derivatives and compounds that are chemically related to gallic acid or including one or more gallic acid moieties. Also included are (precursor) compounds which, after administration, undergo chemical or enzymatic degradation to produce in situ gallic acid, the gallic acid derivative or the compound that is chemically related to gallic acid includes one or more gallic acid containing moieties. Gallic acid derivatives according to the invention include chemical structures derived from gallic acid, such as conjugates, dimers, multimers, salts, esters, ethers, amides etc. Furthermore, the derivatives include those compounds which differ from gallic acid chemically to some degree, such as by the number and/or position of phenolic hydroxyl groups or by the presence of one or more additional substituents, but which have affinity to P-selectin. Examples of other polyhydroxy phenols are: n-dodecyl gallate, caffeic acid and 3,4,5-trihydroxy cinnamic acid.

Likewise, polyphenols have shown to be useful to more or less the same extent as the polyhydroxy phenols, which are gallic acid and derivatives thereof. Polyphenols are defined as compounds, that include more than one 6 carbon atoms-bearing aromatic ring, having one or more hydroxyl groups attached thereto. Examples of such polyphenols are (−)-epigallocatechin gallate, (epi)catechin, m-galloyl gallic acid and ellagic acid.

In this application the polyhydroxy phenols, from which the targeting recognising moiety can be derived, are represented by formula II. Some further explanation about the meaning of the substituents is provided below.

A straight or branched ($C_1$-$C_4$) aliphatic alkyl group exemplifies methyl, ethyl, propyl, isopropyl, butyl, isobutyl and the like. An aromatic group is one having 6 to 14 carbon atoms and comprises a carbocyclic aryl and a heterocyclic aryl group. The carbocyclic aryl group is monocyclic to tricyclic and preferably is phenyl, naphthyl, anthryl, or phenantryl and the like.

The heterocyclic aryl group is a monocyclic to tricyclic group having from 1 to 4 heteroatoms, selected from the group consisting of nitrogen atom, oxygen atom, or sulfur atom. The heterocyclic group is pyrrolyl, pyrazolyl, imidazolyl, thiazolyl, oxazolyl, isothiazolyl, isooxazoryl, 1,3,5-triazolyl, 1,2,4-triazolyl, 1,3,5-thiadiazolyl, 1,3,5-oxadiazolyl, pyrizyl, pyridazinyl, pyrimidyl, pyrazyl, benzofuranyl, isobenzofuranyl, benzothienyl, indolyl, chromenyl, quinolyl, isoquinolyl, phthalazinyl or quionoxalinyl and the like.

The ($C_3$-$C_8$) cycloalkyl group represents cyclopropyl, cyclobutyl, cyclopentyl, cyclohexyl, cycloheptyl or cyclooctyl. Moreover, the ($C_3$-$C_8$) cycloalkyl group is optionally substituted by a straight or branched ($C_1$-$C_4$) aliphatic alkyl group, or one or more carboxylic acid groups.

In a preferred embodiment, polyhydroxy phenols are used which are characterised in that:
$R^1$=ethyl, phenylmethyl, indolylmethyl or 4-hydroxyphenylmethyl;
$R^2$=a straight ($C_1$-$C_4$) aliphatic alkyl group;
$R^3$=a straight ($C_1$-$C_4$) aliphatic alkyl group, substituted by one or two carboxylic acid groups, optionally substituted by a straight or branched ($C_1$-$C_4$) aliphatic alkyl group.

In a more preferred embodiment, polyhydroxy phenols are used wherein:
$R^1$=ethyl, phenylmethyl, indolylmethyl or 4-hydroxyphenylmethyl;
$R^2$=hydrogen, ethyl, propyl or isopropyl
$R^3$=ethylcarboxylic acid or propyldicarboxylic acid.

In order to be effective as targeting ligands, the molecular structures which have affinity to the target P-selectin should be present on or at the surface of the colloidal carriers of the drug delivery system. They may be attached to carrier components covalently or noncovalently. In one of the embodiments, the ligands comprise not only target-recognising structures or moieties, but also a molecular portion which can serve as an anchoring moiety, i.e. which is capable of anchoring the ligand within the carrier, preferably in such a way that the ligand is held in place even though the target recognising moiety extends to—or through—the surface of the carrier. For instance, the anchoring moiety may represent a polymer.

If the colloidal carrier is a liposome, one of the types of ligand which are most useful are conjugates, comprising a peptidic target-recognising moiety and a lipidic anchoring moiety, and optionally a spacer between those moieties.

The anchoring moiety preferably is formed from an amphiphilic lipid, consisting of at least one hydrophobic apolar moiety and a hydrophilic polar head group. The amphiphilic lipid is selected from the group consisting of phospholipids, glycolipids, ceramides, cholesterol and derivatives, saturated or unsaturated, branched or straight chain $C_8$-$C_{100}$ mono- or di-alkyl-amines, arylalkylamines, cycloalkyl alkylamines, alkanols, aldehydes, carbohalides, or alkanoic acids and the anhydrides thereof and characterised in that the total number of C-atoms is 25 or above. Preferably the amphiphilic lipid contains at least two hydrophobic apolar moieties and examples thereof that can be used very favourably are selected from the group consisting of 1-heptadecyl-octadecylamine, N-succinyl-di-octadecylamine and distearylphosphatidylethanol-amine.

The water soluble polymer is a polyethylene glycol, a poly(amino acid), a poly(amino acid derivative), a poly(amino acid analogue), a polyvinylpyrrolidone or ganglioside GM1. For further details with respect to the poly(amino acid)-based polymers, reference is made to WO02/98952, which is herein incorporated by reference.

For instance, a preferred embodiment is the targeting ligand molecule, wherein the target-recognising moiety includes the amino acid sequence XEWVDVY, the lipidic anchoring moiety is represented by a phospholipid residue, and the spacer is a polymer or oligomer. A most preferred embodiment is the molecule XEWVDVY-PEG-DSPE.

A further aspect of the invention relates to a pharmaceutical composition, comprising a colloidal carrier and at least one targeting ligand as described above having affinity to P-selectin associated with the surface of the carrier.

Drug delivery systems are typically advanced pharmaceutical formulations, or formulation components, which generally aim to optimise the delivery of drugs while maximising compliance by favouring simpler and less intrusive delivery methods. Drug delivery systems have been developed for virtually all possible routes of administration. A targeted drug delivery system refers to any formulation or formulation component which effects a more selective delivery of a drug substance to a target within the body. Within the context of the present invention, the target is represented by cells or tissues expressing P-selectin. Therefore, targeted drug delivery implies that the delivery system provides for an increased exposure of the target cells to the drug substance compared with, for instance, a simple solution of the drug substance which is injected intravenously.

An active compound, as used herein, is any therapeutic or diagnostic substance, including natural or artificial mixtures and combinations of substances. Active compounds may be selected from natural, semisynthetic or synthetic small or large molecules, whether organic or inorganic. Active compounds include, for instance, peptides, proteins, nucleic acids such as DNA, RNA, small hairpin RNA, oligonucleotides, and antisense oligonucleotides.

The drug delivery system of the invention specifically comprises (a) a colloidal carrier, (b) an active compound associated with the carrier, and (c) at least one targeting ligand as described above having affinity to P-selectin associated with the surface of the carrier.

The term "colloidal carriers" is used to include all solid, semisolid, or liquid particles or supramolecular structures, or single macromolecules, in the low micron or submicron size range, which is in general the most useful size range for intravascular administration. Examples of colloidal carriers are micro- and nanoparticles, micro- and nanospheres, micro- and nanocapsules, micelles, crosslinked micelles, colloidal hydrogels, complexes, vesicles, such as liposomes and niosomes, virosomes, dendrimers, emulsion droplets, and star polymers. Very suitable carriers are particles or supramolecular structures.

In one of the preferred embodiments, the colloidal carriers of the invention are vesicles and more preferably liposomes, which are fluid-filled vesicles from concentrically assembled layers (typically bilayers) of lipids, such as phospholipids, ceramides, and sterols. Depending on their size and structure, vesicles and/or liposomes are sometimes classified in subcategories, such as small unilamellar vesicles (SUV), large unilamellar vesicles (LUV), multilamellar vesicles (MLV), or giant liposomes, to mention only a few. Liposomes can be designed to have almost any diameter between about 30 nm to several micrometers.

Among the preferred liposomes are those which have a relatively small diameter, such as no more than 1,000 nm, regardless of their lamellarity. The diameter, as used herein, is the mean diameter as assessed by conventional methods known in the art, such as measurements using photon correlation spectroscopy and dynamic light scattering techniques. In another preferred embodiment, the liposomes have a diameter of less than 400 nm, which is a particle size associated with a high physical stability of the respective suspension, or a small tendency of the liposomes to settle or float. Depending on the particular product application or use, it may be useful to limit the diameter of the liposomes (or, if other carriers are used, the diameter of the respective particles or structures) to an even smaller size, such as to no more than 200 nm. For instance, it may be easier to achieve a longer circulation half-life with carriers of this size range.

Liposomes may be prepared from various types of lipids, such as natural, semisynthetic or synthetic phospholipids, sphingolipids, ceramides, sterols, or other lipid-like materials which may be incorporated in lipid bilayers. Preferred lipids are those which are physiologically safe and tolerable, such as neutral (or rather zwitterionic) phospholipids, including phosphatidylcholine (which is a mixture primarily composed of neutral phospholipids), hydrated phosphatidylcholine, lecithin, hydrated lecithin, dimyristoylphosphatidylcholine, distearoylphosphatidylcholine, dipalmitoylphosphatidylcholine, unsaturated phosphatidylcholines having one or two oleic acid chains, optionally mixed with sterols such as cholesterol.

The active compound may be associated with the carrier in various different ways, depending on the actual carrier which is selected, the method of manufacture, and the nature of the active compound itself, especially with regard to the physicochemical properties. For instance, if the carrier is a liposome and the active compound is a lipophilic, poorly soluble molecule, the latter is likely to be primarily associated with the lipophilic regions of the lipid bilayers. On the other hand, if the active ingredient is a soluble hydrophilic substance, it may be encapsulated within the aqueous interior core region of the liposome. If the carrier is a polymeric micro- or nano-particle, the active ingredient may be embedded in the polymeric (or hydrogel) matrix. In core-shell-structures such as micro- or nanocapsules, the active material may be encapsulated within the core. Alternatively, it may be associated with, or bound to the shell, either physicochemically or chemically.

If the drug delivery system is intended for systemic intravascular administration, the chance of specific interaction with the target cells or tissues may be increased if the clearance of the carrier is reduced, as most of the processes collectively termed clearance compete with target interaction. Colloidal particles tend to be cleared rather rapidly from the circulating bloodstream as they are efficiently taken up by the macrophages of the reticuloendothelial system primarily located in the liver and spleen. Depending on the size and the surface properties of colloidal particles, they may be cleared from the circulation with a half-life of minutes. However, by selecting a relatively small particle size and especially by modifying the particle surface, the elimination half-life may be increased to hours, at least. Several polymeric coatings are known which extend the circulation time of liposomes, nanoparticles and other colloidal drug carriers. One of the most efficient polymer coatings known today is composed of polyethylene glycol, or copolymers comprising polyethylene glycol. It is therefore presently a preferred embodiment that the coating of the carriers of the invention comprises polyethylene glycol, or moieties related to polyethylene glycol. However other coatings, based on poly(amino acids), poly(amino acid derivatives), poly(amino acid analogues), polyvinylpyrrolidones and ganglioside GM1, have appeared to be as efficient as polyethylene glycol.

The drug delivery system of the invention is intended as a means for the targeting of drugs to cells or tissues expressing P-selectin, a membrane glycoprotein expressed by vascular endothelial cell and platelets, which is involved in leukocyte adhesion to the endothelium and platelets. It is in particular useful for the targeting to cells or tissues overexpressing P-selectin, or to cells exhibiting increased P-selectin activity. For example, activated endothelial cells present more P-selectin molecules on their cell surfaces. Consequently, the typical pharmacological activity of an active compound which is incorporated in the delivery system and which, according to the invention, is associated with the colloidal carrier, are such that the compound is indicated for the prevention, diagnosis, or treatment for diseases and conditions related to P-selectin activity or overactivity. Among the conditions known today which probably involve P-selectin are coronary artery disease, thrombosis, atherothrombosis, cancer, chronic inflammatory disorders, rheumatoid arthritis, inflammatory bowel disease, multiple sclerosis, atherosclerosis, restenosis, ischemia, reperfusion injury including renal failure, tumour metastasis, bacterial sepsis, disseminated intravascular coagulation, adult respiratory stress syndrome, stroke, angiogenesis, transplant rejection, deep vein thrombosis, myocardial infarction or circulatory shock.

Especially compounds counteracting the inflammatory process within P-selectin activated cells are useful candidates for such drug substances. Anti-inflammatory compounds as defined herein include steroids, particularly glucocorticoids, nonsteroidal anti-inflammatory drugs, and immunosuppressants. In one of the preferred embodiments, the active compound is selected from the group of glucocorticoids, such as dexamethasone, betamethasone, prednisolone, methylprednisolone, cortisone, hydrocortisone, triamcinolone, deflazacort, rimexolone, cloprednol, and fluocortolone.

The targeting to cells expressing or presenting P-selectin is achieved by means of targeting ligands which are associated with the surface of the colloidal carriers, which are comprised in the drug delivery system of the invention. These targeting ligands must have selective affinity to P-selectin. As used herein, "selective" means that the ligands have a higher affinity for P-selectin than for other molecular structures typically found on cell surfaces. In a more narrow sense, selectivity refers to those ligands which have a higher affinity for P-selectin than for other cell adhesion molecules which are related to P-selectin, such as E-selectin. The affinity or binding characteristics of compounds or ligands to P-selectin can be quantified, for example, in terms of the concentration giving 50% inhibition of binding ($IC_{50}$). Typically, a concentration of 50-100 µM or less would be considered as evidence for affinity and binding. More desirable for ligands are substances with values for the concentration giving 50% inhibition of binding of 10 µM or less. The highest values attainable for the non-covalent type bonds playing a role in the interactions or bindings in accordance with the present invention is $10^{-15}$ M. Generally, however, the values are higher than $10^{-12}$ M and in most cases higher than about $10^{-9}$ M.

To ensure a sufficient likelihood of binding between the colloidal carrier and the target molecule P-selectin, there should preferably be at least two targeting ligands associated with the surface of a carrier particle. More preferably, the number of ligands per carrier should be considerably higher than two, such as at least 5, or at least 10. Assuming a random spatial distribution of the ligands over the carrier surface area, the number of ligands per carrier which seems appropriate to ensure a substantial likelihood of interaction with the target would also depend on the diameter of the carrier particle. For instance, small carriers in the range of about 50 to 100 nm may be considered substantially spiked when they are loaded with a number of several dozens to several hundred ligands. Larger carriers in the low micron range, on the other hand, are expected to show significant targeting efficiency when they exhibit at least about a few hundred ligands on their surface. In a preferred embodiment, the carrier particle size is less than 400 nm and the number of targeting ligands per carrier particle is from 20 to 10,000.

The present invention also provides pharmaceutical compositions which comprise a targeted drug delivery system as defined above. Typically, such a pharmaceutical composition will also comprise further excipients, which are selected according to pharmaceutical state-of-the-art formulation techniques.

As used herein, an excipient is any pharmaceutically acceptable substance or mixture of substances having no substantial pharmacological activity, which can be used as a vehicle or as an auxiliary substance to formulate a compound or a drug delivery system into dosage form which is stable and easy to administer. Examples of pharmaceutically acceptable excipients are found in the monographs of all major pharmacopoeias.

In one embodiment, the composition is formulated and processed for parenteral injection, preferably for intravascular injection, such as intravenous or intra-arterial, but also for intramuscular, subcutaneous, intralesional, intraperitoneal or other routes of parenteral administration. The same principles that govern the formulation of other drugs for these administration routes will also teach those skilled in the arts on how to prepare such compositions. For instance, one of the requirements of parenteral dosage forms is their sterility. Other requirements are described in all major pharmacopoeias, such as in USP 24, in the monograph "General Requirements for Tests and Assays. 1. Injections", p. 1775-1777.

To increase the stability of a formulation, it may be necessary to provide a dried dosage form which must be reconstituted before it can be administered. An example of such a dosage form is a freeze-dried or lyophilised formulation. To further increase convenience and safety, the dried dosage form may be combined with an appropriate liquid composition with which it can be reconstituted to form a liquid. In other words, this embodiment of the invention represents a kit for the preparation of a pharmaceutical composition, comprising a solid and a liquid component, wherein the solid component comprises a targeted drug delivery system for delivering an active compound to cells expressing P-selectin as defined above, whereas the liquid component is an aqueous composition. Parenteral formulations are of course within the scope of the invention.

Excipients that are particularly useful for the preparation of parenteral formulations are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolality and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilisers, antioxidants, and preservatives, such as ascorbic acid, sodium sulfite or -hydrogen sulfite, EDTA, benzyl alcohol etc.; other excipients and lyophilization aids, such as albumin, dextran etc.

Alternatively, the pharmaceutical compositions may be designed for oral administration and processed accordingly. Appropriate oral dosage forms include tablets, hard capsules, soft capsules, powders, granules, orally disintegrating dosage forms, syrups, drops, suspensions, effervescent tablets, chewable tablets, oral films, lyophilised dosage forms, sustained release dosage forms, controlled release dosage forms. In one of the preferred embodiments, the oral dosage form is an enterically coated solid dosage form to provide protection of the compound from the acidic and proteolytic environment of the stomach.

It may also be advantageous to administer the targeted drug delivery system of the invention as a transmucosal dosage form or composition. This route of administration is non-invasive and patient-friendly; at the same time it may lead to an improved bioavailability compared to oral administration. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the drug delivery system of the invention is administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases. Presently most preferred, however, are injectable compositions containing the P-selectin targeted drug delivery system.

The following examples are intended to further illustrate the invention, but not to limit its scope to the embodiments presented herein.

EXAMPLES

Example 1

Synthesis of a Peptidic Targeting Ligand Having Affinity to P-Selectin

The human P-selectin binding peptide $H_2N$-DVEWVD-VSY-COOH (Pstar; SEQ ID NO: 1) was synthesised by solid phase chemistry using an Applied Biosystems 9050 peptide synthesizer (Warrington, UK) using standard Fmoc chemistry. The peptide was purified on a C8 RP-column (Alltech, Breda, the Netherlands) using an acetonitrile/water gradient with 0.1% TFA. Sequence and purity were checked by MALDI/LC-MS and size exclusion chromatography using a SMART system (Pep30 column).

In a second step, the peptide was radiolabeled according to the ICl method. Free $^{125}I$ was removed by Sephadex G10 filtration with PBS as eluent. Purity was checked by SDS-PAGE gel electrophoresis (20%) and analysed using a phosphor imager. The peptide was stored at 4° C. in PBS.

In a third step, the radiolabeled peptide was dissolved in HEPES buffer (Biosolve, Valkenswaard, the Netherlands) (10 mM HEPES, pH 6.6), and N-hydroxy-succimidyl poly(ethylene glycol distearoyl-phosphatidylethanolamine (MW 3400) (DSPE-PEG$_{3400}$-NHS: 7 equivalents) (Shearwater Polymers Inc., Huntsville, U.S.A.) was added to this solution in several portions. After gentle stirring at room temperature for 18 hours, the remaining NHS groups were quenched through the addition of glycine. The formation of the conjugate DSPE-PEG-($^{125}I$)-Pstar was determined by SDS-PAGE gel electrophoresis (20%) and SMART-analysis using a Pep30 or Superose 6 column with PBS (0.02% NaN$_3$ and 1 mM EDTA (Roche Molecular Biochemicals)) as eluent.

Example 2

Preparation of a Liposomal Drug Delivery System Comprising Dexamethasone

Liposomes were prepared by means of extrusion. In short, egg yolk phosphatidylcholine (Lipoid, Ludwigshafen, Germany) (EYPC; 100 mg/ml in MeOH/CHCl$_3$, v/v 1:1) and cholesterol (10 mg/ml in MeOH/CHCl$_3$ v/v 1:1) were mixed in a weight ratio of 5.0:0.44 (mg/mg) and the mixture was dried under a stream of nitrogen. After hydration of the lipids in 2 ml buffer (0.1 M KCl, 10 mM Tris-HCl, pH 8.0), the suspension was extruded 31 times through a Whatman Nuclepore polycarbonate membrane (100 nm, Pleasanton, Calif.) using a LiposoFast-pneumatic (Cavestin Inc., Ottawa, Canada). Particle size was determined by photon correlation spectroscopy (Malvern 4700 C System, Malvern Instruments, Malvern, UK) at 27° C. and a 90° angle between laser and detector (65-73 nm, polydispersity 0.1-0.27). The phosphatidylcholine content of the liposomes was determined enzymatically using the Roche Molecular Biochemicals enzymatic kit for phospholipids, with Precipath L (Roche Molecular Biochemicals) as an internal standard. Fluorescently labeled liposomes were prepared by addition of 1,1'-dioctadecyl-3,3,3',3'-tetramethylindocarbocyanide (Molecular Probes, Leiden, the Netherlands) (DiI; 1% in MeOH/CHCl$_3$, V/V 1:1) to the crude lipid mix. Dexamethasone phosphate (10 mg) was added to the sonication buffer to obtain the dexamethasone phosphate containing liposomes.

In a subsequent step, the targeting ligand DSPE-PEG-($^{125}I$)-Pstar (as prepared according to example 1) was associated with the liposomes. The desired amounts of DSPE-PEG$_{3400}$-($^{125}I$)-P-star and poly(ethylene glycol) distearoylphosphatidylethanolamine (MW 2000) (Shearwater Polymers Inc, Huntsville, U.S.A.) (DSPE-PEG$_{2000}$; 5 mole % in total) were incorporated by incubation with the liposomes at 37° C. for 2 hours. The number of associated conjugate per 70 nm liposome was calculated assuming 1.12× 10$^{11}$ liposomes/mg of phospholipids. Liposomes containing 100 (LP$_{100}$) and 500 (LP$_{500}$) were prepared. For preparation of control liposomes (P0), the same amount of DSPE-PEG-NHS quenched with glycine was added. A sample of these liposomes were then subjected to SMART analysis using a Superose 6 column at 50 μl/min with PBS, with 10 mM EDTA and 0.02% $NaN_3$ as eluent.

Example 3

Evaluation of Affinity

The affinity of the liposomal drug delivery system prepared in example 2 was evaluated using a competition assay. TM11-PO, a tetrameric TM11/strepPO complex described by Molenaar et al. (Blood 100: 3570-3577 (2002)), was freshly prepared by incubating streptavidin-peroxidase (Amersham Life Science, Little Chalfont, United Kingdom) (strep-PO; 8.4 μl, 2.0 μM) and biotin-CDVEWVDVSSLEWDLPC (SEQ ID NO: 2; synthesized by Dr. Vander Zee, Department of Immunology, University of Utrecht, Utrecht, the Netherlands) (TM11-biotin; 1.5 μl 190 mM) for 2 hours at room temperature in assay buffer (20 mM HEPES, 150 mM NaCl, 1 mM $CaCl_2$, pH 7.4). For competition studies, a 96 wells microtiter plate (high binding, flat bottom, Costar, Corning, U.S.A) was coated overnight at 4° C. with 10 μg/ml goat anti-human IgG (Sigma-Aldrich, Zwijndrecht, the Netherlands) in coating buffer (50 mM $NaHCO_3$, pH 9.6). Subsequently, wells were washed with assay buffer and incubated for 1 hour at 37° C. with blocking buffer (3% BSA in assay buffer). After washing with assay buffer the wells were incubated for 2 hours at 37° C. with human P-selectin/IgG-Fc (R&D Systems Europe Ltd., Abingdon, United Kingdom) (0.3 μg/ml). Subsequently, wells were washed with assay buffer and incubated for 1 hour at 4° C. with the TM11-PO complex. The wells were washed six times with washing buffer (0.1% Tween 20 in assay buffer). 3,3',5,5'-Tetramethylbenzamidine (TMB)/hydrogen peroxide ($H_2O_2$) (Pierce, Rochford, U.S.A.) was added and wells were incubated at room temperature for 15 minutes. The reaction was halted by addition of 2 M $H_2SO_4$ and the absorbance was measured at 450 nm. In result, the $P_{100}$ and $P_{500}$ liposomes showed a much higher affinity ($IC_{50}$=0.78 and 0.34 nM, respectively) for P-selectin than both control liposomes without targeting ligands, which showed no affinity, and free Pstar, which displayed a low micromolar affinity ($IC_{50}$=7 μM).

Example 4

Evaluation of Targeting Properties

The targeting properties of the liposomal drug delivery system prepared in example 2 was evaluated using a cell culture model. As a measurement of the targeting efficiency of dexamethasone-loaded $P_{100}$ and $P_{500}$ liposomes, their capacity to induce corticosteroid responsive gene expression was measured and compared to liposomes without ligands ($P_0$).

Human CHO-cells, stably transfected with human P-selectin (CHO-P cells, generous gift from Dr. Modderman, University of Amsterdam, Amsterdam, the Netherlands) were grown in DMEM containing 10% foetal calf serum (BioWhittaker, Verviers, Belgium), 5 mM L-glutamine, 20,000 units penicillin/streptomycin (BioWhittaker, Verviers, Belgium) and 5 mM non-essential amino acids. Culture flasks were incubated at 37° C. in 5% $CO_2$ for 3 or 4 days until cells had grown to confluence. Cells were seeded in 24 wells culture plates (ca. 100,000 cells per well) and grown to 90% confluence in steroid-free DMEM (10% FCS). The cells were transfected by incubation for 5 hours with a freshly prepared Lipofectin mixture containing a reporter gene construct encoding glucocorticoid responsive element-driven Firefly luciferase (Clontech) ($TAT_3$-Luc gene; 10 ng/well), pCMV-Luc encoding Renilla luciferase (Promega) (0.1 ng/well) and empty vector was added up to 1 μg DNA/well in Optimem. The CMC-driven Renilla luciferase was added to correct for transfection efficiency. The transfection mixture was removed and steroid-free DMEM was added to the cells. After 18 hours $P_{500}$ liposomes (1 nM, with or without dexamethasone phosphate), control $P_o$ (1 nM) or dexamethasone phosphate (1 μM were added to the cells and left to incubate for 5 hours. The medium was removed and the cells were washed with PBS. After incubation with lysis buffer, the Renilla and Firefly luciferase activity were measured simultaneously using a Dual Luciferase Assay kit (Promega).

Luciferase expression was observed 5 hours after transfection: relative transfection was increased 5-fold with dexamethasone-laden $P_{500}$ as compared to $P_0$ and $P_{500}$ without dexamethasone. At a 1 nM liposome concentration, these liposomes have a comparable effect on luciferase activity as free dexamethasone at 1 μM concentration.

The invention claimed is:

1. The targeting ligand molecule DVEWVDVSY (SEQ ID NO: 1)-PEG-DSPE.

2. A pharmaceutical composition comprising (a) a carrier and (b) at least one targeting ligand molecule according to claim 1 associated with the surface of the carrier.

3. The pharmaceutical composition according to claim 2, wherein the carrier is a colloidal carrier composed of particles selected from vesicles, such as liposomes and niosomes, nanocapsules, microcapsules, nanoparticles, microparticles, micelles, or is a lipid complex, a colloidal hydrogel or a micro-emulsion.

4. The pharmaceutical composition according to claim 3, wherein the particles of the colloidal carrier have a mean diameter of less than 1 µm.

5. The pharmaceutical composition according to claim 4, wherein the particles of the colloidal carrier have a mean diameter of less than 400 nm.

6. The pharmaceutical composition according to claim 3, wherein the carrier is composed of liposomes.

7. The pharmaceutical composition according to claim 3, wherein it contains a pharmacologically active agent or a diagnostic agent.

8. The pharmaceutical composition according to claim 7, wherein the pharmacologically active agent is an agent for the prevention or treatment of a disease or condition, in which P-selectin is involved, selected from coronary artery disease, thrombosis, atherothrombosis, cancer, chronic inflammatory disorders, rheumatoid arthritis, inflammatory bowel disease, multiple sclerosis, atherosclerosis, restenosis, ischemia, reperfusion injury including renal failure, tumour metastasis, bacterial sepsis, disseminated intravascular coagulation, adult respiratory distress syndrome, stroke, angiogenesis, transplant rejection, circulatory shock, deep vein thrombosis or myocardial infarction.

9. The pharmaceutical composition according to claim 3, wherein the carrier comprises a coating providing for decreased uptake of the composition by cells of the reticuloendothelial system.

10. The pharmaceutical composition according to claim 9, wherein the coating of the carrier comprises one or more water soluble polymers.

11. The pharmaceutical composition according to claim 10, wherein the water soluble polymer is selected from the group consisting of polyethylene glycols, poly (amino acids), poly (amino acid derivatives), poly (amino acid analogues), polyvinylpyrrolidones and ganglioside GM1.

12. The pharmaceutical composition according to claim 3, wherein the composition comprises DVEWVDVSY-PEG-DSPE (SEQ ID NO: 1).

13. The pharmaceutical composition according to claim 3, wherein it contains at least 2 targeting ligand molecules.

14. The pharmaceutical composition according to claim 3, wherein it contains at least 10 targeting ligand molecules.

15. The pharmaceutical composition according to claim 3, wherein it contains from 20 to 10,000 targeting ligand molecules.

16. The pharmaceutical composition according to claim 3, wherein the composition is administered by oral, parenteral, transmucosal or pulmonary route.

17. The pharmaceutical composition according to claim 16, wherein the composition is administered by the parenteral route.

18. A kit for the preparation of the pharmaceutical composition according to claim 3, the kit comprising a liquid and a solid component, the liquid component being an aqueous composition and the solid component comprising: (a) a colloidal carrier and (b) at least one targeting ligand molecule, and being prepared by conventional methods and subsequent removal of the water.

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Asp Val Glu Trp Val Asp Val Ser Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: synthesized protein for use in competition
      assay

<400> SEQUENCE: 2

```
Cys Asp Val Glu Trp Val Asp Val Ser Ser Leu Glu Trp Asp Leu Pro
1               5                   10                  15
Cys
```